US00PP32719P2

(12) United States Plant Patent
Cervantes Mantilla et al.

(10) Patent No.: US PP32,719 P2
(45) Date of Patent: Jan. 5, 2021

(54) MANGO TREE NAMED 'MAGRIVER'

(50) Latin Name: *Mangifera indica*
Varietal Denomination: Magriver

(71) Applicant: MAGDALENA RIVER COLOMBIA S.A.S., Malambo (CO)

(72) Inventors: Mónica Isabel Cervantes Mantilla, Barranquilla (CO); Furio Ricciardiello, Barranquilla (CO)

(73) Assignee: MAGDALENA RIVER COLOMBIA S.A.S., Malambo (CO)

( * ) Notice: Subject to any disclaimer, the term of this patent is extended or adjusted under 35 U.S.C. 154(b) by 0 days.

(21) Appl. No.: 16/501,793

(22) Filed: Jun. 7, 2019

(51) Int. Cl.
*A01H 5/08* (2018.01)
*A01H 6/00* (2018.01)

(52) U.S. Cl.
USPC ..... Plt./159

(58) Field of Classification Search
USPC ..... Plt./156, 159
See application file for complete search history.

(56) References Cited

PUBLICATIONS

Bally. 2006. *Mangifera indica* (mango). Species Profiles for Pacific Island Agroforestry. 25 pages (Year: 2006).*

* cited by examiner

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of mango tree (*Mangifera indica*), 'Magriver', is disclosed which is distinguished by the production of heavy and consistent crops of fruit that are 168 g average weight, having a rounded base, stool stem inserted obliquely in a level manner, a rounded apex with a small lateral beak, and undulating surface. The tree is corpulent and its shape is erect, open, and branched. It is a vigorous tree and highly productive, with good disease tolerance. The fruit skin color is bright yellow with small pink or crimson blush, and thin tender and adhesive skin. The flavor is excellent, rich and aromatic, with a strong component of sugar cane, a creamy smooth texture with a brix of 15.5°±1 and a long flavor-life in storage. The new 'Magriver' tree is adapted to soils with salinity.

3 Drawing Sheets

Genus and species: *Mangifera indica.*
Variety denomination: 'Magriver'.

BACKGROUND OF THE NEW PLANT

The present invention comprises a new and distinct variety of mango tree, botanically known as *Mangifera indica*, and hereinafter referred to by the variety name 'Magriver'.

'Magriver' is a new variety of mango tree discovered as a seedling that was derived from open-pollination of mango tree named 'Hilacha' (unpatented) and was selected for remarkable qualities when compared with 'Hilacha'. Selection of the new variety was made in 2016 in the municipality of Sitionuevo, Magdalena Department, Colombia, South America, and was made based on improved characteristics including disease resistance, brighter color, and adaptability to soils with salinity. Asexual propagation of the new variety by grafting using cuttings and one-year-old rootstock was first performed in 2016 at the Magdalena Farm in Colombia, South America.

The new 'Magriver' variety is distinguished by the production of heavy and consistent crops of fruit which are 168 g average weight, with a rounded base, stool stem inserted obliquely in a level manner, a rounded apex with a small lateral beak, and undulating surface. The tree is corpulent and its shape is erect, open, and branched. It is a vigorous tree and highly productive, with good disease tolerance. The fruit skin color is bright yellow with small pink or crimson blush, with thin, tender and adhesive skin. The flavor is excellent, rich and aromatic, with a strong component of sugar cane, a creamy smooth texture with a brix of 15.5°±1 and a long flavor-life in storage. The new 'Magriver' tree is adapted to soils with salinity.

The new 'Magriver' tree has been asexually propagated via grafting using cuttings and has been found to retain its distinctive characteristics through asexual propagations.

Plant Breeder's Rights for this variety have not been applied for. The new variety 'Magriver' has not been made publicly available or sold anywhere in the world more than one year prior to the effective filing date of this application.

SUMMARY OF THE INVENTION

The following are the most outstanding and distinguishing characteristics of this new cultivar when grown in Colombia, South America and can be used to distinguish 'Magriver' as a new and distinct variety of mango tree:

1. Heavy and consistent crops of fruit;
2. Excellent disease tolerance;
3. Adapted to soils with salinity;
4. Suitable as a rootstock; and
5. Excellent quality for juice and pulp.

DESCRIPTION OF THE PHOTOGRAPHS

This new mango tree is illustrated by the accompanying photographs which show the entire tree, the inside and outside of the fruit, and the seed; the colors shown are as true as can be reasonably obtained by conventional photographic procedures. The photographs are of a 2-year-old tree grown in Colombia, South America, taken in July 2017.

DESCRIPTION OF THE NEW VARIETY

Figure 1:
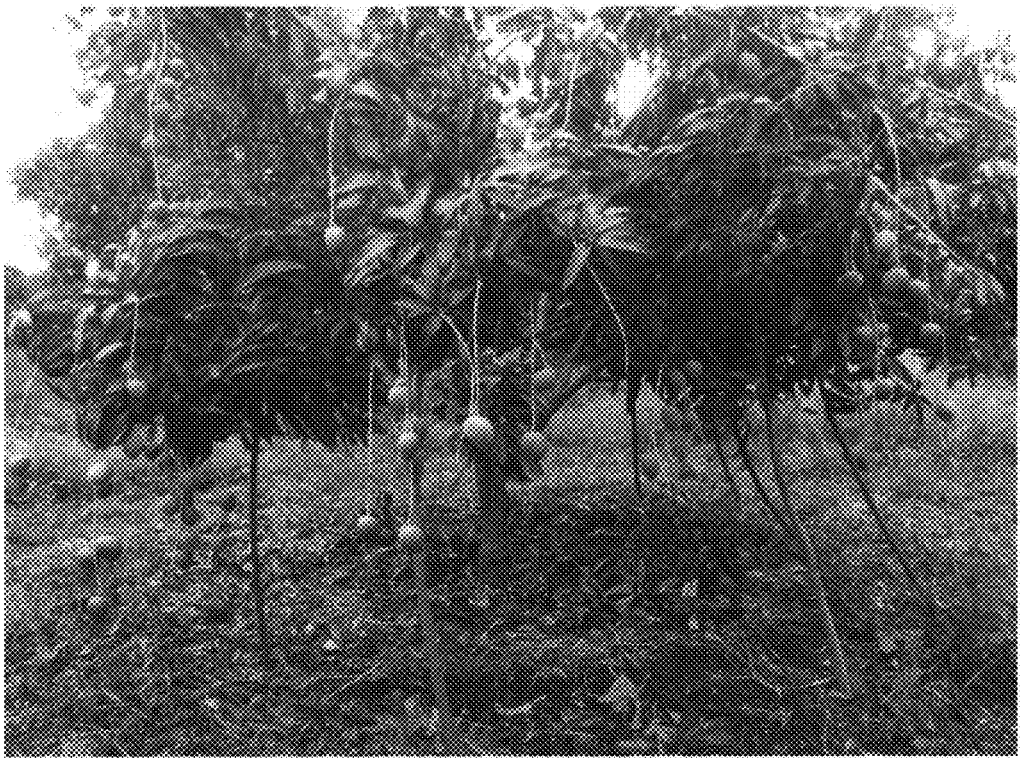
FIG. 1 shows the entire tree.
Figure 2:
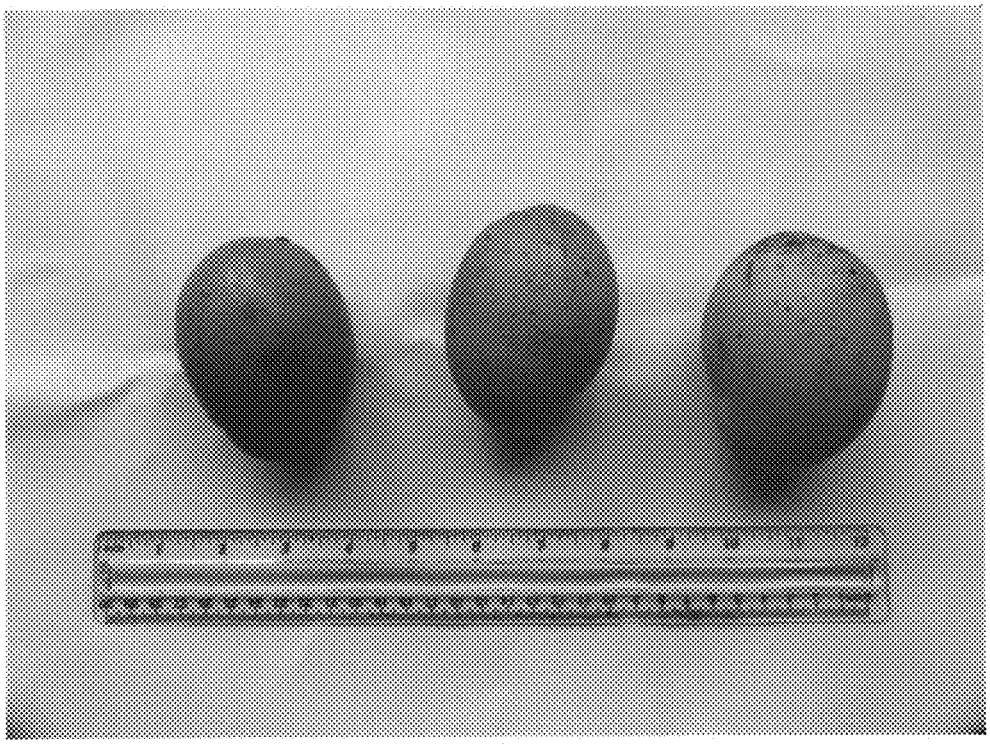
FIG. 2 shows the exterior of the immature and mature fruit.
Figure 3:
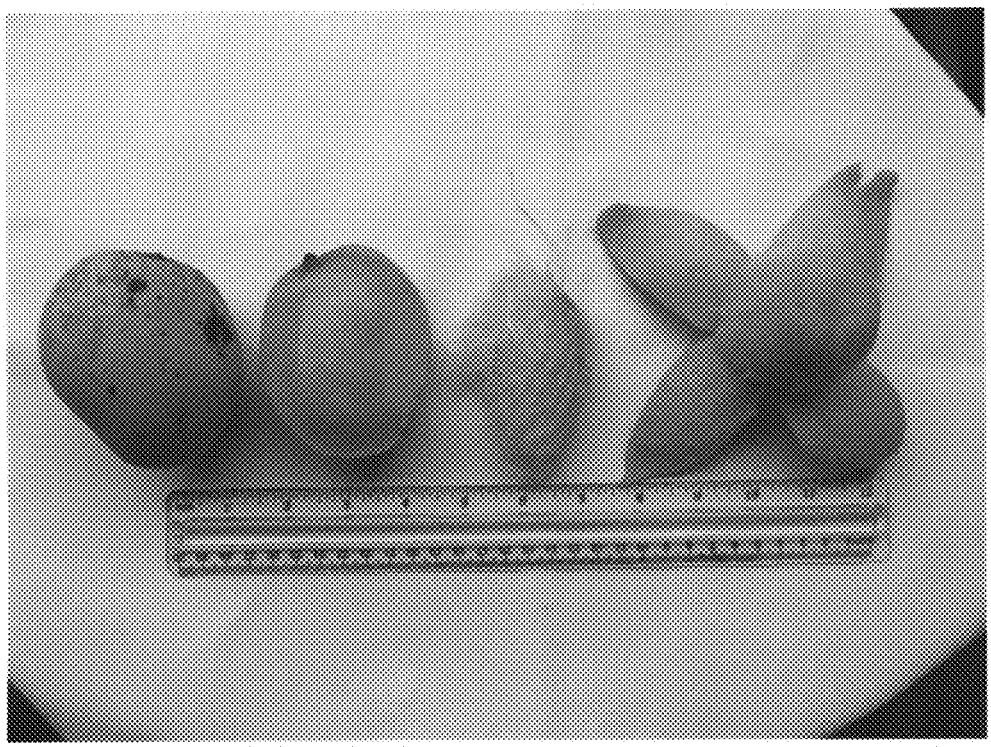
FIG. 3 shows the interior of the mature fruit.
Figure 4:
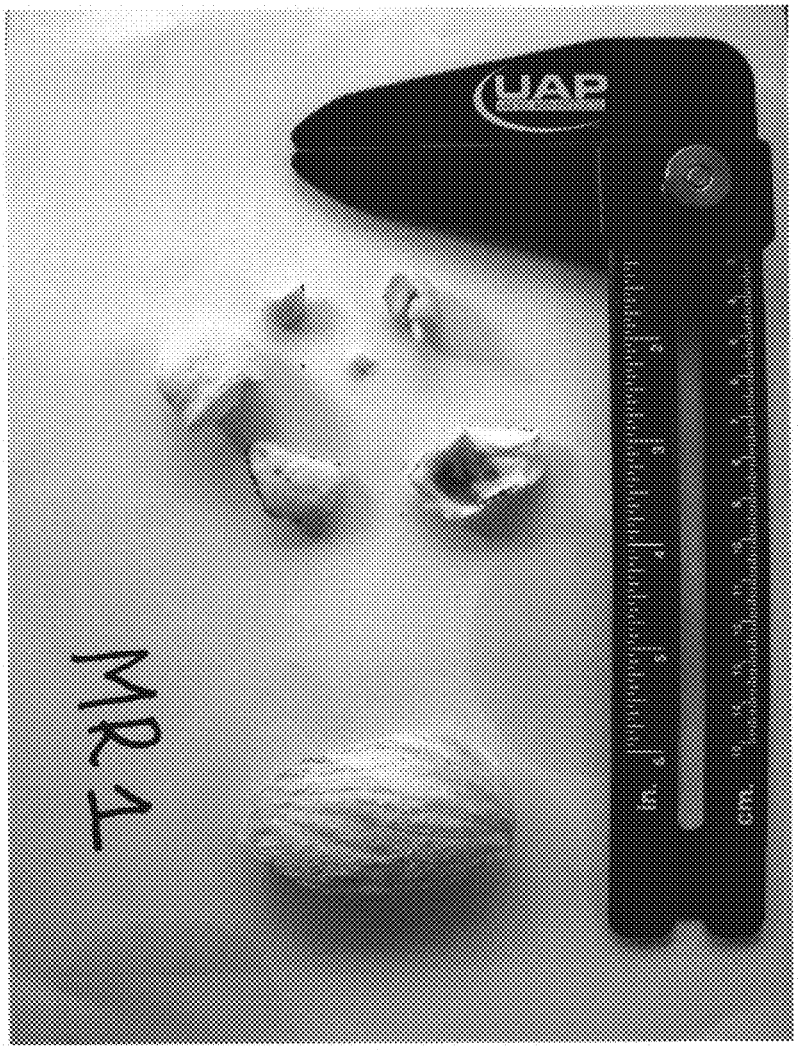
FIG. 4 shows the seed.

The following detailed descriptions set forth the distinctive characteristics of 'Magriver'. Trees of the new mango variety have not been observed under all possible environmental conditions. Observations and measurements were taken on a 2-year-old tree grown outdoors in Colombia, South America, in July 2017. The farm where 'Magriver' was selected and asexually propagated is affected by saline soils and high amount of chlorides and sulfates of calcium, magnesium and sodium. The saline soils and higher pH do not affect the new 'Magriver' trees as compared to other new introductions to the area. The soils are 32% clay, 57% slime, and 11% sand, and the temperatures range from 23° C. to 38° C. Precipitation in the region varies throughout the year, with the lowest in February with 0 mm and the highest in October with 192 mm. The annual average relative humidity varies between 79% and 81%. Color readings were taken under natural light. Color references are primarily to The R.H.S. Colour Chart of The Royal Horticultural Society of London (R.H.S.) (2016 edition).

DETAILED BOTANICAL DESCRIPTION

Classification:
- *Family*.—Anacardiaceae.
- *Botanical name*.—*Mangifera indica*.
- *Denomination*.—'Magriver'.

Tree:
- *Growth habit*.—Spreading and columnar.
- *Height*.—2.6 m high.
- *Regularity of bearing*.—Regular bearing.
- *Productivity*.—Very good; 120.0 kg per tree.

Trunk:
- *Diameter*.—28.0 cm.
- *Surface texture*.—Smooth and regular.
- *Color*.—Gray to tan, consistent with trunk color of other mango varieties (approximately RHS 199A).

Branches:
- *Habit*.—Spreading and open.
- *Size*.—Variable.
- *Surface texture*.—Smooth and regular.
- *Color* (*one year old and older*).—Same as trunk.

Leaves:
- *General size*.—Very large compared with other mango varieties.
- *Length*.—17.0 cm.
- *Width*.—8.0 cm.
- *Shape*.—Lanceolate.
- *Apex*.—Acute with some twisting.
- *Base*.—Broad angular.
- *Margin*.—Smooth to slightly wavy.
- *Shape in cross-section*.—Incurved.
- *Pubescence*.—Absent.
- *Color*.—Upper surface: Pea green (RHS 139B). Lower surface: Typically the same as upper (Pea green), or with a slightly more yellow tint (RHS 153C).
- *Petiole*.—Length: 4.0 cm to 5.0 cm. Diameter: 0.3 cm to 0.4 cm. Color (mature): Gray (RHS 201B). Color (immature): Brown (RHS 177B).

Inflorescence:
- *General*.—Flowers produced on terminal inflorescences with thousands of individual flowers that typically set less than 1.5% in natural pollination.
- *Pollinator information*.—Main pollinators are flies.
- *Date of bloom*.—Mid-December to early March.

Flower bud:
- *Length*.—2.5 mm.
- *Surface texture*.—Surface is firm.

Flowers: Flowers have high percentage of hermaphrodite flowers (50% to 70%) compared with other cultivars.
- *Petals and sepals*.—Both male and hermaphrodite flowers have 5 petals and sepals. Flowers are both male and hermaphrodite.
- *Width*.—2.5 mm.
- *Width when fully open*.—4.3 mm.
- *Petals*.—Quantity per flower: 5. Color: White to cream gray (RHS 155A) to brown (RHS 178B) with maturity.
- *Sepals*.—Quantity per flower: 5.
- *Peduncle*.—Small and many-branched. Color: Pink to brown (RHS 178B).

Reproductive organs:
- *Anther quantity*.—5 per flower.
- *Anther color*.—White (RHS 155A).
- *Ovary quantity*.—1.

Fruit:
- *General*.—The fruit are ripe for commercial harvesting and shipment approximately April through July in Barranquilla, Colombia. The fruit are small, but with variation in sizes.
- *Length*.—Typical average length: 7.1 cm. Smallest average length: 6.5 cm. Largest average length: 7.5 cm.
- *Diameter*.—Typical average diameter: 6.0 cm. Smallest average diameter: 5.0 cm. Largest average diameter: 6.5 cm.
- *Thickness*.—Typical average thickness: 6.1 cm. Smallest average thickness: 6.0 cm. Largest average thickness: 6.5 cm.
- *Weight*.—Typical average weight: 168.0 g. Smallest average weight: 150.0 g. Largest average weight: 172.0 g.
- *Shape*.—Oblong to oval with an undulating skin surface, a rounded base, slender stem with a squared insertion, no cavity, and a bluntly rounded apex with a large lateral beak.
- *Surface*.—Slightly wavy.
- *Appendix*.—Lightly dotted.
- *Peak*.—Small; side.
- *Shape of peak*.—Bluntly pointed.
- *Stem*.—Peduncle: Hard; cylindrical. Length: 10.0 cm to 16.0 cm. Diameter: 0.3 cm. Color: Brown to gray (RHS 199C).
- *Skin*.—Thickness: Thin, tender and adhesive. Smoothness: Moderately undulating. Lenticels: Few, small, yellow lenticels (RHS 162B). Color: Yellow-orange (RHS 21A), with an orange to pink blush (RHS 32B) if fruit is exposed to the sun.
- *Flesh*.—Texture: Soft, melting and juicy with fiber. Color: Yellow-orange (RHS 24A). Fiber: Present. Flavor: Excellent flavor reminiscent of melon, citrus, and sugar cane; best flavor is obtained when tree ripened; rich, aromatic and sweet with a strong component of sugar cane and a brix content of 15.5°±1. Fragrance: Slight and pleasant.

*Seed*.—General: Polyembryonic; suitable as rootstock in saline soils. Shape: Oblong-oval. Length: 6.7 cm. Breadth: 3.58 cm. Thickness: 1.98 cm. Weight: 22.0 g. Texture: Thick and woody; tied to the pulp.

*Softening*.—Time to softening (ripening) depends on stage of maturity (3 to 10 days); softening is uniform and rapid once it begins; yet, flesh firmness is maintained for several days at room temperature.

*Use*.—Mango pulp and juice.

*Keeping quality*.—Above average shipping and shelf life.

*Harvesting*.—By hand.

Disease resistance:

*Anthracnose* (*colletotricum gloeosporioides*).—Good tolerance.

*Powdery mildew* (*oidium mangiferae*).—Moderate susceptibility.

Physiological conditions: Sap burn is not a problem in Colombia.

COMPARISON WITH PARENTAL AND SIMILAR COMMERCIAL VARIETY

The new 'Magriver' variety differs from the parent tree 'Hilacha' (unpatented) in that 'Magriver' produces fruit that are oblong to oval with a rounded base and no cavity, having an average weight of 168 g and a brix value of 15.5°±1, and is suitable for rootstock in saline soils, while 'Hilacha' produces fruit that varies in shape with some being more elongated and some rounded, with a cavity in the base, having an average weight of 150 g and a brix value of 19, and is not suitable for rootstock in saline soils. Additionally, the flowers, fruit, and branches of 'Magriver' have low symptoms of anthracnosis (*Colletotricum gloeosporioides*), whereas the flowers, fruit, and branches of 'Hilacha' are extremely sensitive to the disease when grown under the same environmental conditions in Colombia.

'Magriver' differs from commercial mango variety 'Haden' (unpatented) in that 'Magriver' produces small fruit with an oblong to oval shape, whereas 'Haden' produces medium to large fruit with an oval to round shape.

I claim:

1. A new and distinct variety of mango tree named 'Magriver', substantially as described and illustrated herein.

* * * * *